United States Patent [19] [11] Patent Number: 4,797,478
Lebuhn et al. [45] Date of Patent: Jan. 10, 1989

[54] PROCESS FOR PRODUCING COLOR-STABLE, INDUSTRIAL-GRADE METHYL GLUCOSIDE

[75] Inventors: Rolf Lebuhn; John Feldmann; Hubert Koebernick, all of Krefeld, Fed. Rep. of Germany

[73] Assignee: CPC International Inc., Englewood Cliffs, N.J.

[21] Appl. No.: 29,496

[22] Filed: Mar. 23, 1987

[30] Foreign Application Priority Data

Apr. 2, 1986 [DE] Fed. Rep. of Germany ....... 3611035

[51] Int. Cl.$^4$ ........................ C07H 1/00; C07H 15/04; C07G 3/00
[52] U.S. Cl. ................................ 536/18.5; 536/18.6; 536/124
[58] Field of Search ..................... 536/18.5, 124, 18.6, 536/1.1

[56] References Cited

U.S. PATENT DOCUMENTS

| | | | |
|---|---|---|---|
| 2,606,186 | 8/1952 | Dean et al. | 536/18.6 |
| 3,450,690 | 6/1969 | Gibbons et al. | 536/18.5 |
| 3,928,318 | 12/1975 | Panusch et al. | 536/18.6 |
| 4,223,129 | 9/1980 | Roth et al. | 536/4.1 |
| 4,329,449 | 5/1982 | Roth et al. | 536/18.6 |
| 4,349,669 | 9/1982 | Klahr et al. | 536/124 |
| 4,465,828 | 8/1984 | Rau et al. | 536/124 |
| 4,483,979 | 11/1984 | Mao | 536/18.5 |
| 4,510,306 | 4/1985 | Langdon | 536/124 |
| 4,704,453 | 11/1987 | Lorenz et al. | 536/124 |

Primary Examiner—Ronald W. Griffin
Assistant Examiner—Nancy S. Carson

[57] ABSTRACT

A process for producing an industrial-grade methyl glucoside with improved color stability. Glucose is reacted in two steps with methanol and a higher-boiling alcohol at elevated temperatures in the presence of an acidic, preferably heterogeneous catalyst, under as dry as possible conditions.

22 Claims, No Drawings

PROCESS FOR PRODUCING COLOR-STABLE, INDUSTRIAL-GRADE METHYL GLUCOSIDE

FIELD OF THE INVENTION

This invention relates to a process for producing a color-stable, industrial-grade methyl glucoside with a very low content of residual glucose.

BACKGROUND OF THE INVENTION

Methyl glucoside is a well-known industrial chemical which has been employed in the preparation of surfactants and as a plasticizer for various resins. Polyether polyols derived from methyl glucoside and other glucosides are particularly suitable as intermediates for the production of polyurethanes.

The preparation of methyl glucoside by the reaction of glucose with methanol in the presence of acid catalysts has long been known. U.S. Pat. No. 2,606,186 discloses the use of a cation exchange resin as a catalyst to replace the more typical mineral acid catalyst in the reaction. Typical resins employed were sulfonated-type cation exchangers including sulfonated phenolformaldehyde cation-exchange resins, sulfonated polystyrene cation-exchange resins, and sulfonated coal-type cation-exchange resins. It was necessary to isolate the product by crystallization in order to obtain material of suitable purity for use.

U.S. Pat. No. 3,928,318 discloses a modified method for preparation of methyl glucoside. In this disclosure, the procedure involved heating a mixture of glucose and methanol with sulfuric acid catalyst in the presence of a large amount of anhydrous calcium sulfate to remove water from the reaction mixture. A pressure vessel was also employed. Other commercial processes have used polysaccharides, such as starch, instead of glucose as the starting material.

Alkyl glucosides in general and methyl glucoside in particular are known to have poor alkali stability when they are produced on an industrial scale. This presents a problem when the glucosides are used for such applications as intermediates for the production of polyether polyols for polyurethane foams, since the reactions are carried out under alkaline conditions. The reaction of glucose with an alcohol, in particular methanol, in the presence of an acid catalyst according to known methods invariably yields a reaction product with poor stability in the presence of alkalis. This poor stability is caused by relatively high content of unconverted glucose and side-reaction products irrespective of whether a homogeneous or a heterogeneous acid catalyst is used. For this reason, industrial-grade methyl glucoside cannot be used directly for the most important applications. It must be subjected to troublesome, costly purifying and stabilizing treatment with bases or basic anion-exchange resins or by fractional crystallization.

SUMMARY OF THE INVENTION

It is, therefore, an object of the present invention to provide an improved method for the production of methyl glucoside which overcomes the disadvantages of previous methods and gives an industrial-scale production of methyl glucoside which can be used as a starting or intermediate product for further reactions under alkaline conditions. A particular object is to provide for the production of methyl glucoside useful for preparing polyurethanes, without the need to subject it to troublesome, costly and loss-involving stabilizing and purifying treatments.

In accordance with this invention, there is provided a process for producing a color-stable, industrial-grade methyl glucoside which comprises:

(a) first heating a mixture of glucose and methanol in the presence of an acidic catalyst under conditions which exclude water until the reaction product mixture contains less than about 20% glucose on a dry weight basis;

(b) then heating the reaction product mixture with a higher-boiling alcohol in the presence of an acidic catalyst under conditions for the continuous azeotropic removal of water until the glucose content of the mixture is about 0.3% or less on a dry substance basis; and (c) separating unreacted higher-boiling alcohol from the mixture obtained in Step (b).

Also provided, in accordance with this invention, is a process for producing a color-stable, industrial-grade methyl glucoside which comprises:

(a) heating a mixture of glucose and a higher-boiling alcohol in the presence of an acidic catalyst under conditions for the continuous azeotropic removal of water until the glucose content of the reaction product mixture measured as a D.E. value is below about 0.2% on a dry weight basis;

(b) separating unreacted alcohol from the reaction product mixture of Step (a); and (c) reacting the mixture obtained in Step (b) with methanol in the presence of an acidic catalyst until the methyl glucoside content of the resulting product is at least 60% on a dry weight basis.

DETAILED DESCRIPTION OF THE INVENTION

Methyl glucoside containing less than about 0.3% by weight residual glucose is made by reacting glucose with methanol in the presence of an acid catalyst in a two-step process. While the process of the invention may use homogeneous catalysts, it is preferable to employ heterogeneous, preferably solid, acid catalysts which upon completion of the reaction can be easily removed. Such catalysts may be reused several times after regeneration. They have proved to be especially suitable in the methylating step.

Preferred solid acid catalysts are acidic, preferably inorganic, molecular sieves, and, in particular, strongly acidic cation-exchange resins. Highly cross-linked macroporous resins, like Amberlyst 15 ® and Lewatit SPC 118 ®, as well as slightly cross-linked gel resins, like SC 104 ®, have been found to be particularly active catalysts.

It has been discovered that the catalyst concentration has a considerable influence on the ratio of alpha- to beta-glucosides in the product. When the catalyst concentration is lowered, the proportion of beta-glucoside rises. This influence of the concentration of heterogeneous catalysts on the ratio of alpha- to beta-glucosides in the reaction product mixture is quite surprising since U.S. Pat. No. 4,329,449 indicates that catalyst concentration does not influence the alpha:beta ratios.

The observed effect with heterogeneous catalysts may be due to a catalysis of the anomerizing reaction in which the glucoside first formed reacts with alcohol molecules with inversion at the anomeric center. The beta-glucosides, which are more unstable, react at a higher rate than the alpha-glucosides. In the process of the invention, this effect may be used to advantage to produce industrial-grade methyl glucoside with a relatively low proportion of glucosides of the higher-boiling alcohols. This is done by selecting the conditions in the first step, if methanol is reacted there, so as to promote the formation of alpha-glucoside. In the alternate process, where a higher-boiling alcohol is used in the first step, conditions are changed to promote the formation of beta-glucoside.

A high proportion of alpha-glucoside in the product of the first step inhibits a transglucosidizing reaction in the second step. This is useful when the reaction with methanol takes place in the first step and transglucosidization is undesirable in the second step. A high proportion of beta-glucoside promotes the transglucosidizing reaction, which is desired if the reaction with methanol takes place in the second step.

The reaction can also be significantly influenced by appropriate selection of the excess of alcohol used. A high alcohol excess not only reduces the oligosaccharide portion formed in the product by side-reactions, but also, in combination with other measures of the process of the invention, raises the yields of monomer alkyl glucoside to values of up to 95%, based on the glucose used. Such yields are substantially above the levels given for most known processes. Moreover, it surprisingly permits changing the ratio of alpha- to beta-glucoside, since the proportion of beta-glucoside in the reaction product mixture rises as the amount of alcohol is increased. Use of 3 to 20 moles of alcohol per mole of glucose or transglucosidizable glucoside have proved to be particularly advantageous.

During the reaction with the higher-boiling alcohol, the water formed is preferably removed from the reaction mixture continuously by distillation in order to promote glucoside formation. It is, therefore, preferred to use higher-boiling alcohols of the type that form an azeotrope with water, or to add an inert entrainer, such as benzene or toluene, to the reaction mixture to form an azeotrope with water, and, possibly, with the higher-boiling alcohol.

For the purposes of this invention, a higher-boiling alcohol is one that boils above about 80° C. at atmospheric pressure. Higher-boiling alcohols preferred for the purposes of the invention are propanol, ethylene glycol, and, in particular, butanol.

Although water in principle impairs the formation of glucoside and the highest possible degree of dryness should therefore be maintained during operation, it does not need to be totally excluded in the process of the invention. As shown in the example for the formation of the glucoside of butanol, neither the required reaction nor the process control are overly impaired by water when present in the batch at a concentration of up to 10% by weight. Thus, when forming the glucoside of butanol, the butanol phase, which forms during separation of the condensed azeotrope and contains 20% water, may be recycled to the reaction mixture without drying if a high butanol excess is used and the butanol-water azeotrope is continuously distilled off. Water contents of more than 10% in the reaction medium prolong the reaction time considerably, however.

According to a preferred embodiment of the invention, a solid, preferably inorganic, water-adsorbing agent, which is practically insoluble in the reaction medium, is added to the reaction mixture. This is particularly preferable in the first step of glucoside formation where a comparatively large amount of reaction water accumulates. This water-adsorbing agent promotes glucoside formation by binding water which cannot be removed by distillation. The water-adsorbing agent may be separated easily from the reaction product after completion of the reaction. It can then be dried and reused. Particularly preferred water-adsorbing agents are inorganic, acidic molecular sieves, which also act as catalysts.

Since drying is of advantage mainly in the final phase of the reaction and/or in cases where the water content of the reaction mixture cannot be kept low by distillation, a solid water-adsorbing agent is used preferably in the methylating step. This applies especially when methylating is the first of the two reaction steps characterizing the process of the invention. It has been found advantageous not to add the water-adsorbing agent until the reaction has reached an advanced stage and is slowed down by the approach to the dynamic equilibrium and the accumulation of reaction water. For the purposes of the invention, the water-adsorbing agent is therefore added to the reaction medium, preferably during the final phase of the methylating step when a methyl glucoside content of at least 65%, preferably at least 75%, and more preferably at least 80%, on a dry weight basis (without catalyst), has been reached.

It is noted in this connection that the process of the invention can be carried out not only in batches, but also continuously. The catalyst and/or the water-adsorbing agent may thus be arranged in one or several bed(s) through which the reaction mixture is passed, instead of being dispersed in the reaction medium.

A preferred embodiment of the invention produces a low-cost industrial-grade methyl glucoside in high yields that is color-stable to alkali. Glucose is reacted with methanol in the first step until the reaction product mixture contains at least 80%, preferably at least 90%, and more preferably at least 95% methyl glucoside, on a dry weight basis. This reaction is preferably performed under conditions which promote the formation of alpha-methyl glucoside rather than of beta-methyl glucoside. Unreacted methanol and water is removed from the reaction product mixture. The reaction product mixture thus obtained is then reacted with the higher-boiling alcohol in a second step until the residual glucose content of the reaction product mixture is at most 0.3%, preferably at most 0.2%, and more preferably not more than 0.15%, on a dry weight basis measured as a D.E. value.

Another variation of the process of the invention produces low-cost, industrial-grade methyl glucoside with high yields of methyl glucoside in the final product. Glucose is first reacted with methanol. An intermediate product featuring a higher total content of methyl glucoside(s) and higher ratio of alpha- to beta-methyl glucoside is obtained by concentration and precipitation. When this precipitated product is treated with a higher-boiling alcohol in the second step, the transglucosidation of methyl glucoside with higher-boiling alcohol is greatly reduced.

Another parameter by which the reaction can be controlled is the reaction temperature. It permits selectively adjusting the proportion of monomer glucopyranosides in the product. This proportion first increases with increasing reaction temperature due to the higher rate of glucose conversion and the transformation of the furanosides developed under kinetically-controlled conditions into pyranosides. It then drops at higher temperatures due to an increased formation of oligomer glucosides. The reaction of glucose with butanol shows an increasing amount of monomer glucopyranosides up to about 130° C. This is largely similar to that shown by other alcohols. Also, the ratio of alpha- to beta-glucoside increases as the temperature rises. For the reaction with higher-boiling alcohols, the reaction temperature may be adjusted within a relatively wide range by an appropriate selection of the pressure in the reactor. For the reaction with methanol, it is, in most cases, suitable to use normal pressure under reflux.

The examples illustrate the two variants of the process of the invention, i.e., further glucosidation of methyl glucoside raw material and transglucosidation of high-quality glucoside of a higher-boiling alcohol with methanol, using butanol as the example of a higher-boiling alcohol preferred for the purposes of the invention.

In the examples, the color stability of the product under alkaline conditions and under heat is determined as follows:

Color Stability Under Alkaline Conditions

The alkali stability is measured in aqueous 70% solutions. In the presence of 7% potassium hydroxide, the solution is heated for 1 hour to 80° C., whereupon the color of the sample is determined according to the Gardner scale.

Color Stability Under Heat

The heat stability is measured in aqueous 70% solutions. The sample is exposed for 4 hours to a temperature of 160° C. in an open container. Distilled water is added to replace water lost before the color of the sample is determined according to the Gardner scale.

EXAMPLE 1

In a 1-liter three-necked flask with reflux condenser and stirrer, 240 g anhydrous dextrose, 540 g methanol and 60 g of a highly acidic cation exchanger (Amberlyst 15 ®) were mixed at approximately 1000 rpm and heated under reflux. After 10 hours, 40 g of a molecular sieve of 3 Å pore size was added and the batch was heated under stirring for another 2 hours under reflux. The resulting nearly colorless solution was filtered while still hot, catalyst resin and molecular sieve were separated by sifting, and the filtrate was concentrated to dryness. The resulting methyl glucoside (250 g) showed a content of reducing sugars measured as dextrose equivalent (D.E.) of 5.1%.

Before the second reaction step, this crude glucoside was transferred to a flask with drip funnel, stirrer, distilling bridge and thermometer. After adding 1050 g butanol and 30 g Amberlyst 15 ®, the solution was heated under stirring to a temperature of the liquid body of 90° C. and the butanol-water azeotrope distilled off at a vacuum of 300 mbars, while the liquid volume in the reaction flask was kept constant by adding butanol drop by drop. After a reaction time of 1.5 hours, the solution was filtered while hot, neutralized with 1 N caustic soda solution and the solvent was distilled off; the small amounts of methanol present in the distillate may be separated from the butanol by distillation.

The syrupy residue was dissolved in water and decolorized with the aid of activated carbon. After evaporation of the water, the final product had a D.E. value of 0.07.
Color stability under alkaline conditions: 7.0
Color stability under heat: 0.4

According to HPLC analysis, 65% methyl glucoside and 35% butyl glucoside were present in the final product. The proportion of monomer glucopyranoside (DP1) was 87%.

EXAMPLE 2

In a reactor with reflux condenser and stirrer, 5 kg anhydrous dextrose, 4.5 kg methanol and 1.5 g of highly acid cation-exchange resin (Lewatet SPC 11 ®; dry) were mixed and heated under reflux. After a reaction time of 12 hours, the product showed a D.E. value of 8.0 and was removed from the catalyst by filtering. The solution was concentrated by distilling off 2.5 kg methanol and the residue was cooled down to room temperature. A white precipitate (1.3 kg) resulted, which was separated by centrifuging and subjected to an analysis which showed a D.E. value of 1.5 and a content of methyl-alpha-D-glucopyranoside of 92%. Two hundred fifty g of this product was transferred to a flask with drip funnel, stirrer, distilling bridge and thermometer, and blended with 1050 g butanol and 25 g cation-exchange resin (Lewatit SPC 118 ®). The solution was heated under stirring and at a temperature of the liquid body of 80°–90° C. and a vacuum of 300 mbars. A butanol-water azeotrope was distilled off, while butanol was continuously added to the reaction batch drop by drop in order to keep the liquid volume constant. After a reaction time of 2 hours, the solution was filtered while hot, neutralized with 1 N caustic soda solution and butanol was distilled off.

The residue was dissolved in water and decolorized with the aid of activated carbon. After concentrating, the final product had a D.E. value of 0.08.
Color stability under alkaline conditions: 7.2
Color stability under heat: 0.4

According to HPLC analysis, 94% methyl glucoside and 6% butyl glucoside were present in the final product. The proportion of monomer glucopyranoside (DP$_1$) was 94%.

EXAMPLE 3

In a three-necked flask with reflux condenser and stirrer, 240 g anhydrous dextrose, 540 g methanol and 70 g acid cation-exchange resin (Amberlyst 15 ®) were mixed and heated under reflux. After a reaction time of 10 hours, the solution was filtered while hot and concentrated to dryness. The D.E. value of the resulting crude methyl glucoside (250 g) was 9.5.

In a flask with drip funnel, stirrer, distilling bridge and thermometer, the glucoside was blended with 880 g ethylene glycol and 37 g cation-exchange resin (Amberlyst 15 ®). At a temperature of the liquid body of 75° C. and a vacuum of 3 mbars, the reaction water was separated from the stirred batch by distillation; any codistilled ethylene glycol was replaced drop by drop. After a reaction time of 1.5 hours, the solution was filtered while hot, neutralized with 1 N caustic soda solution and the alcohol was distilled off. The residue was dissolved in water and decolorized with the aid of activated carbon and concentrated. The final product showed a D.E. value of 0.10.
Color stability under alkaline conditions: 8.5
Color stability under heat: 0.8

According to HPLC analysis, 71% methyl glucoside and 29% hydroxyethyl glucoside were present in the final product. The proportion of monomer glucopyranoside (DP$_1$) was 95%.

EXAMPLE 4

In a flask with drip funnel, stirrer, distilling bridge and thermometer methyl glucoside (250 g) produced as in Example 3 was mixed with 850 g n-propanol and 45 g cation-exchange resin (Amberlyst 15). At a temperature of the liquid body of 83° C. and a vacuum of 700 mbars, propanol-water azeotrope was distilled off, the volume of the reaction batch being kept constant by adding n-propanol drop by drop. After a reaction time of 1.5 hours, the solution was separated from the cation exchanger by filtering, neutralized with 1 N caustic soda solution and the alcohol was distilled off. The residue was dissolved in water, decolorized with the aid of activated carbon and concentrated to dryness. The D.E. value of the resulting product was found to be 0.05.
Color stablity under alkaline conditions: 6.3
Color stability under heat: 0.3

According to HPLC analysis, 78% methyl glucoside and 22% propyl glucoside were present in the final product. The proportion of monomer glucopyranoside ($DP_1$) was 95%.

EXAMPLE 5

In a flask with drip funnel, stirrer, distilling bridge and thermometer, 80 g anhydrous dextrose, 300 g n-butanol and 10 g of a highly acid cation-exchange resin (Amberlyst 15®) were mixed (approximately 1000 rpm) and heated to a temperature of the liquid body of 90° C. At a vacuum of 300 mbars, the reaction water was distilled off as azeotrope and the liquid volume in the reaction flask kept constant by adding n-butanol drop by drop. After a reaction time of 6 hours, the solution was filtered while hot and the butanol distilled off. The butyl glucoside (100 g) obtained as residue showed a D.E. value of 0.10 and contained 53% n-butyl-alpha-D-glucopyranoside and 37% n-butyl-beta-D-glucopyranoside.

In the second reaction step, the butyl glucoside was blended with 170 g dried methanol and 30 g cation-exchange resin (Amberlyst®) and under stirring heated under reflux. After a reaction time of 10 hours, the solution was filtered while hot, neutralized with 1 N caustic soda solution, the methanol distilled off at normal pressure and the n-butanol at reduced pressure. The residue was dissolved in water and decolorized with the aid of activated carbon. The product thus obtained as final product showed a D.E. value of 0.15.
Color stability under alkaline conditions: 10.0
Color stability under heat: 0.9

According to HPLC analysis, 67% methyl glucoside and 33% butyl glucoside were present in the final product. The proportion of monomer glucopyranoside ($DP_1$) was 84%.

Thus, there has been provided, in accordance with this invention, a process for preparing an industrial grade of methyl glucoside which meets the aims and objectives set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for producing a color-stable, industrial-grade methyl glucoside which comprises:
   (a) first heating a mixture of glucose and excess methanol in the presence of an acidic catalyst under conditions which exclude water until the reaction product mixture contains less than about 20% glucose on a dry weight basis;
   (b) then heating the reaction product mixture with an excess of a higher-boiling alcohol in the presence of an acidic catalyst under conditions for the continuous azeotropic removal of water until the glucose content of the mixture is about 0.3% or less on a dry substance basis, said higher-boiling alcohol being one that boils above 80° C. at atmospheric pressure and forms an azeotrope with water; and
   (c) separating unreacted higher-boiling alcohol from the mixture obtained in Step (b).

2. The process of claim 1 wherein the acidic catalyst is a heterogeneous acidic catalyst.

3. The process of claim 2 wherein the heterogeneous acidic catalyst is a strongly acidic cation-exchange resin.

4. The process of claim 3 wherein the strongly acidic cation-exchange resin is selected from the group consisting of: a highly cross-linked macroporous resin, a slightly cross-linked gel resin, and an acidic molecular sieve.

5. The process of claim 4 wherein the acidic molecular sieve is an inorganic molecular sieve.

6. The process of claim 2 wherein the heterogeneous acidic catalyst is solid under reaction conditions.

7. The process of claim 1 wherein the methanol is used at a molar ratio to glucose of from 3:1 to 20:1.

8. The process of claim 1 wherein, during the reaction with the higher-boiling alcohol, an inert entrainer is used which forms an azeotrope with water.

9. The process of claim 1 wherein the higher-boiling alcohol is selected from the group consisting of: propanol, ethylene glycol, and butanol.

10. The process of claim 1 wherein the unreacted methanol and water is removed from the reaction product mixture of Step (a) before Step (b) is carried out.

11. The process of claim 1 wherein a water-absorbing agent, which is practically insoluble in the reaction mixture, is used in the reaction between glucose and methanol.

12. The process of claim 11 wherein the water-absorbing agent is added to the reaction mixture in the final phase of Step (a) when a methyl glucoside content of at least 65%, on a dry weight basis, has been reached.

13. The process of claim 12 wherein the water-absorbing agent is added to the reaction mixture in the final phase of Step (a) when a methyl glucoside content of at least 75%, on a dry weight basis, has been reached.

14. The process of claim 12 wherein the water-adsorbing agent is added to the reaction mixture in the final phase of Step (a) when a methyl glucoside content of at least 80%, on a dry weight basis, has been reached.

15. A process for producing a color-stable, industrial-grade methyl glucoside which comprises:
   (a) heating a mixture of glucose and excess of a higher-boiling alcohol in the presence of an acidic catalyst under conditions for the continuous azeotropic removal of water until the glucose content of the reaction product mixture measured as a D.E. value is below about 0.2% on a dry weight basis, said higher-boiling alcohol being one that boils above 80° C. at atmospheric pressure and forms an azeotrope with water;
(b) separating unreacted alcohol from the reaction product mixture of Step (a); and
(c) reacting the mixture obtained in Step (b) with an excess of methanol in the presence of an acidic catalyst until the methyl glucoside content of the resulting product is at least 60% on a dry weight basis.

16. The process of claim 15 wherein the acidic catalyst is a heterogeneous acidic catalyst.

17. The process of claim 16 wherein the heterogeneous acidic catalyst is a strongly acidic cation-exchange resin.

18. The process of claim 17 wherein the strongly acidic cation-exchange resin is selected from the group consisting of: a highly cross-linked macroporous resin, a slightly cross-linked gel resin, and an acidic molecular sieve.

19. The process of claim 18 wherein the acidic molecular sieve is an inorganic molecular sieve.

20. The process of claim 16 wherein the heterogeneous acidic catalyst is solid under reaction conditions.

21. The process of claim 15 wherein, during the reaction with the higher-boiling alcohol, an inert entrainer is used which forms an azeotrope with water.

22. The process of claim 15 wherein the higher-boiling alcohol is selected from the group consisting of: propanol, ethylene glycol, and butanol.

* * * * *